United States Patent
Sherry et al.

(10) Patent No.: US 9,726,548 B2
(45) Date of Patent: Aug. 8, 2017

(54) TERAHERTZ IMAGER

(71) Applicant: STMicroelectronics SA, Montrouge (FR)

(72) Inventors: Hani Sherry, Grenoble (FR); Andreia Cathelin, Laval (FR); Andreas Kaiser, Villeneuve D'Ascq (FR); Ullrich Pfeiffer, Wuppertal (DE); Janusz Grzyb, Hilden (DE); Yan Zhao, Los Angeles, CA (US)

(73) Assignee: STMicroelectronics SA, Montrouge (FR)

( * ) Notice: Subject to any disclaimer, the term of this patent is extended or adjusted under 35 U.S.C. 154(b) by 105 days.

(21) Appl. No.: 14/925,753

(22) Filed: Oct. 28, 2015

(65) Prior Publication Data
US 2016/0047692 A1 Feb. 18, 2016

Related U.S. Application Data

(63) Continuation of application No. 14/024,481, filed on Sep. 11, 2013, now Pat. No. 9,176,009.

(30) Foreign Application Priority Data

Sep. 12, 2012 (FR) .................................... 12 58573

(51) Int. Cl.
| | | |
|---|---|---|
| *G01J 5/22* | (2006.01) | |
| *G01J 5/10* | (2006.01) | |
| *G01N 21/3581* | (2014.01) | |
| *G01J 5/20* | (2006.01) | |
| *H01Q 23/00* | (2006.01) | |
| *G01J 5/00* | (2006.01) | |

(52) U.S. Cl.
CPC . *G01J 5/22* (2013.01); *G01J 5/10* (2013.01); *G01N 21/3581* (2013.01); *G01J 5/20* (2013.01); *G01J 2005/0077* (2013.01); *G01J 2005/202* (2013.01); *H01Q 23/00* (2013.01); *Y10T 29/49018* (2015.01)

(58) Field of Classification Search
CPC ........ G01J 5/22; G01J 5/10; G01J 5/20; G01J 2005/0077; G01J 2005/202; G01N 21/3581
See application file for complete search history.

(56) References Cited

U.S. PATENT DOCUMENTS

| | | |
|---|---|---|
| 5,420,547 A | 5/1995 | Kikuchi |
| 5,764,111 A | 6/1998 | Bushman |

(Continued)

FOREIGN PATENT DOCUMENTS

WO 2011029742 A1 3/2011

OTHER PUBLICATIONS

French Search Report received in Application No. 1258572 mailed Jul. 25, 2013, 7 pages.

(Continued)

*Primary Examiner* — Christine Sung
(74) *Attorney, Agent, or Firm* — Slater Matsil, LLP (57) ABSTRACT

A terahertz imager includes an array of pixel circuits. Each pixel circuit has an antenna and a detector. The detector is coupled to differential output terminals of the antenna. A frequency oscillator is configured to generate a frequency signal on an output line. The output line is coupled to an input terminal of the antenna of at least one of the pixel circuits.

26 Claims, 4 Drawing Sheets (56) References Cited

U.S. PATENT DOCUMENTS

| | | | |
|---|---|---|---|
| 2006/0239688 A1* | 10/2006 | Hillis | B82Y 20/00 |
| | | | 398/116 |
| 2007/0285246 A1 | 12/2007 | Koyama | |
| 2010/0253440 A1 | 10/2010 | Li et al. | |
| 2011/0001173 A1 | 1/2011 | Ojefors et al. | |
| 2012/0075034 A1 | 3/2012 | Afshari et al. | |
| 2013/0082785 A1 | 4/2013 | Afshari et al. | |
| 2014/0048710 A1 | 2/2014 | Xu et al. | |
| 2014/0070893 A1 | 3/2014 | Sherry et al. | |
| 2014/0091376 A1* | 4/2014 | Boppel | H01L 31/101 |
| | | | 257/291 |

OTHER PUBLICATIONS

"ISSCC 2009/Session 11/TD: Trends in Wireless Communications/11.4," IEEE International Solid-State Circuits Conference, Jul. 27, 2009, 3 pages.

Ka-Fai Un, et al., "Analysis and Design of Open-Loop Multiphase Local-Oscillator Generator for Wireless Applications," IEEE Transactions on Circuits and Systems, vol. 57, No. 5, May 2010, 12 pages.

Lisauskas, A. et al., "Terahertz imaging with Si MOSFET focal-plane arrays," Terahertz Technology and Applications II, vol. 7215, downloaded from: http://ebooks.spiedigitallibrary.org on Jul. 16, 2013, 12 pages.

Momeni, O., et al., "High Power Terahertz and Millimeter-Wave Oscillator Design: A Systematic Approach," IEEE Journal of Solid-State Circuits, vol. 46, No. 3, Mar. 2011, 15 pages.

"Ring oscillator," en.wikipedia.org/wiki/Ring_oscillator, downloaded Apr. 17, 2013, 3 pages.

* cited by examiner

TERAHERTZ IMAGER

This is a continuation application of U.S. application Ser. No. 14/024,481, entitled "Terahertz Imager" which was filed on Sep. 11, 2013 and is incorporated herein by reference. This application also claims priority to French Patent Application 1258573, filed Sep. 12, 2012 and is incorporated herein by reference.

TECHNICAL FIELD

The present disclosure relates to the field of terahertz imagers, and in particular embodiments to a terahertz imager and method of receiving a terahertz signal using an array of pixel elements.

BACKGROUND

A terahertz imager is an image sensor adapted to capture an image of a scene based on waves in the terahertz frequency range. In general, terahertz waves are considered to comprise waves having a frequency of between 300 GHz and 3 THz. These frequencies for example correspond to wavelengths of one millimeter or less. For example, a 1 THz wave has a wavelength of approximately 300 µm.

Terahertz imagers are used widely for applications in which it is desirable to "see through" certain materials. In particular, terahertz waves have good penetrability in many dielectric materials and non-polar liquids. They are however almost entirely reflected by metals and absorbed by water molecules. This makes terahertz imagers particularly suited for applications such as in the security scanners used at airports and in devices used to analyze works of art. The wavelength is in general short enough to achieve good spectral resolution for imaging, but long enough such that the waves are scattered relatively little by air particles such as dust or smoke.

In general, terahertz imagers use a terahertz source to illuminate the scene to be captured. This is because the presence of natural terahertz radiation is generally relatively low.

It has been proposed to provide a fully integrated terahertz camera based on silicon technology. However, there are technical difficulties in implementing such a camera, due at least in part to the relatively high frequency of the terahertz signal range, and the relatively low energy of the signal to be captured. Furthermore, it would be desirable to adapt terahertz imagers to permit them to additionally capture image depth and/or to improve the image quality.

SUMMARY OF THE INVENTION

Embodiments of the present invention at least partially address one or more problems in the prior art.

According to one aspect, a terahertz imager comprises: an array of pixel circuits, each pixel circuit having an antenna and a detector. The detector is coupled to differential output terminals of the antenna. A frequency oscillator is configured to generate a frequency signal on an output line. The output line is coupled to an input terminal of the antenna of at least one of the pixel circuits.

According to one embodiment, the antenna comprises an annular conductor. The differential output terminals are positioned at opposite points around the annular conductor and the input terminal is positioned at a point of equal distance from each of the differential output terminals.

According to another embodiment, the differential output terminals are positioned on an inner edge of the annular conductor and the input terminal is positioned on an outer edge of the annular conductor.

According to another embodiment, the frequency signal is at a frequency in the range of 300 GHz to 3 THz.

According to another embodiment, the detector of each of the pixel circuits comprises a first transistor having a first of its main current terminals coupled to a first of the differential output terminals of the antenna and a second transistor having a first of its main current terminals coupled to a second of the differential output terminals of the antenna.

According to another embodiment, a second main current terminal of the first transistor is coupled to a first column line of the pixel array and a second main current terminal of the second transistor is coupled to a second column line of the pixel array.

According to another embodiment, a second main current terminal of each of the first and second transistors is coupled to an output node of the pixel circuit, the output node being coupled to a column line of the pixel array and to a capacitor.

According to another embodiment, the frequency oscillator comprises a first ring oscillator formed of an odd number N of inverters coupled in series where N is equal to three or more. An output from a first of the inverters is coupled to the output line of the frequency oscillator via a first filter and an output from a second of the inverters is coupled to the output line of the frequency oscillator via a second filter. For example, the first and second filters are each adapted to filter out at least the fundamental frequency component present at the output nodes of the first and second inverters.

According to another embodiment, the first and second filters have cut-off frequencies selected based on the frequency of the Nth harmonic present at the outputs of the inverters.

According to another embodiment, the first and second filters each have a lower cut-off frequency falling between the (N−2)th and the Nth harmonic present at the outputs of the inverters and a higher cut-off frequency falling between the Nth and (N+2)th harmonic present at the outputs of the inverters.

According to another embodiment, the frequency oscillator further comprises a second ring oscillator formed of N inverters coupled in series, wherein at least one first line connecting a pair of inverters of the first ring oscillator is positioned alongside at least one second line connecting a pair of inverters of the second ring oscillator, such that electromagnetic coupling occurs between the first and second lines.

According to another embodiment, N is equal to 5 or 7.

According to another embodiment, the terahertz imager further comprises a transmission antenna for transmitting terahertz radiation. The terahertz transmission antenna is coupled to the output line of the frequency oscillator.

According to a method embodiment, a pixel circuit of a terahertz imager can be formed. The method comprises forming an antenna of the pixel circuit; forming a detector of the pixel circuit; coupling the detector to differential output terminals of the antenna; and coupling an input terminal of the antenna to an output line of a frequency oscillator.

BRIEF DESCRIPTION OF THE DRAWINGS

The foregoing and other purposes, features, aspects and advantages of the invention will become apparent from the following detailed description of embodiments, given by way of illustration and not limitation with reference to the accompanying drawings, in which.

DETAILED DESCRIPTION OF ILLUSTRATIVE EMBODIMENTS

Figure 1:
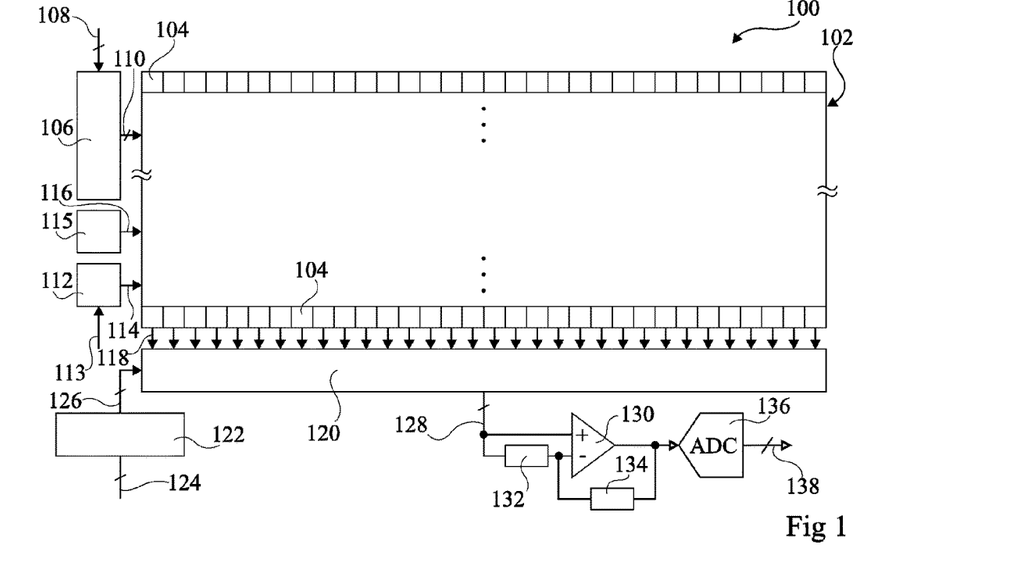
FIG. 1 illustrates a terahertz imager according to an example embodiment of the present disclosure.

FIG. 1 schematically illustrates a terahertz imager 100 according to an example embodiment.

The imager 100 comprises an image sensor formed of a 2-dimensional array 102 of pixel circuits 104. In the example of FIG. 1, the array 102 comprises 1024 pixel circuits arranged in 32 rows and 32 columns. Of course, it will be apparent to those skilled in the art that the pixel array 102 could be of a different size and/or aspect ratio. For example, the array 102 could comprise between 2 and several hundred rows and between 2 and several hundred columns of pixels.

The pixel array 102 is for example controlled in a similar fashion to the pixel array of a visible light image sensor. In particular, a row decoder 106 is for example provided, which receives a row selection signal on an input line 108. The row selection signal indicates a row to be read during a read phase of the pixel array 102. The row decoder 106 provides a corresponding control signal to a row line (not illustrated in FIG. 1) of each row of the pixel array 102. For example in the case that there are 32 rows, the row selection signal is 5 bits wide.

A control block 112 is also for example provided, which receives a control signal on input line 113 for controlling the timing of a global shutter of the pixel array, as will be described in more detail below. The control block 112 provides a corresponding control signal on an output line 114 to each pixel circuit 104 of the pixel array 102.

Furthermore, as will be described in more detail below, a frequency oscillator circuit 115, which may be positioned on-chip or off-chip, for example supplies a frequency signal to each pixel circuit 104 of the pixel array 102.

The pixel array 102 for example, provides output signals on outputs 118, each comprising one or more column lines associated with each column of the pixel array 102. The outputs 118 are coupled to an output block 120 comprising active loads for driving each column line as well as switches for selecting columns, as will be described in more detail below.

In one embodiment, the columns are read in sequence, under control of a column decoder 122. The column decoder 122 receives a column selection signal on input lines 124. Assuming that the pixel array 102 comprises 32 columns, the column selection signal on line 124 is for example 5 bits wide. The column decoder 122 provides a corresponding control signal on output lines 126 to control one or more switches of the output block 120 associated with each column of the pixel array 102.

The output block 120, for example, provides an output on output lines 128, of which there are one or more output lines associated with each column. The output block 120 provides an analog voltage level representing the values read from the pixel circuit of a selected row and column. The analog voltage values are for example provided to one or more output amplifier circuits. In the example of FIG. 1, an example of an amplifier circuit comprising an amplifier 130, for example an operational amplifier, is illustrated. A positive input of the amplifier 130 is coupled to the output lines 128, and the negative input of amplifier 130 is coupled to the output lines 128 via a resistor 132. The negative input is also coupled to the output of the amplifier 130 via a resistor 134. The output of the amplifier 130 is further coupled to an analog to digital converter (ADC) 136, which generates a digital value on output lines 138 based on the analog input voltage read from the pixel array 102. For example, the ADC is a ramp converter, which is well known in the art.

In alternative embodiments, the columns could be read in parallel, an amplifier and an ADC being provided for each column.

Of course, the amplifier circuit at the output of the pixel array could be implemented in many different ways as will be appreciated by those skilled in the art, the circuit illustrated in FIG. 1 being only one example.

Figure 2:
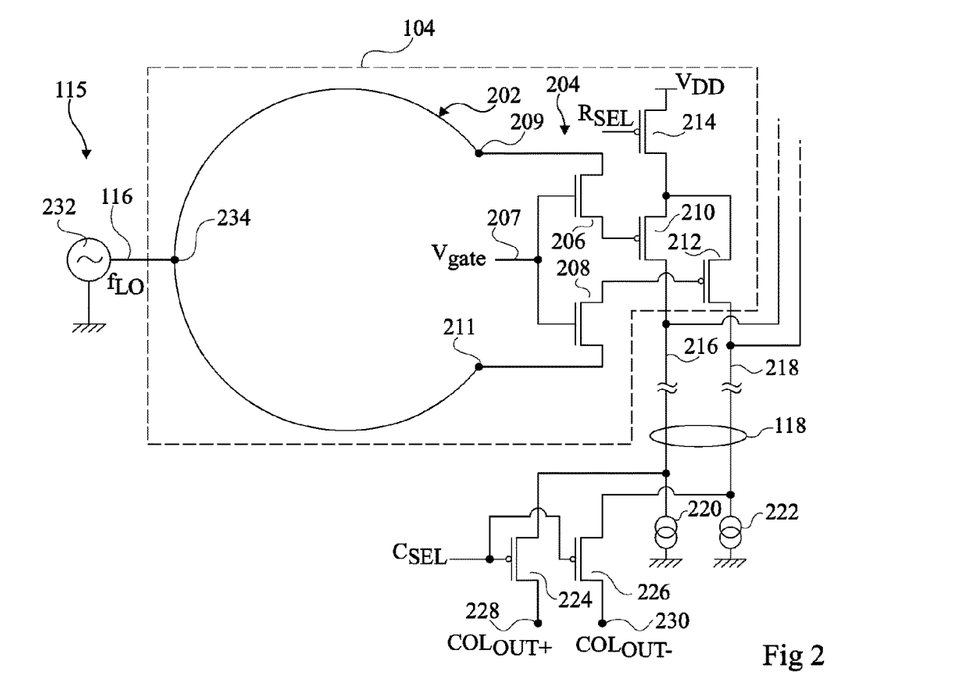
FIG. 2 illustrates a pixel circuit of a pixel array of the terahertz imager of FIG. 1 in more detail according to an example embodiment of the present disclosure.

FIG. 2 schematically illustrates an example of one of the pixel circuits 104 of the pixel array 102 in more detail according to an example embodiment, along with column lines and output circuitry.

Each pixel circuit 104, for example, comprises an antenna 202 having differential outputs coupled to a detector 204. The detector 204 comprises transistors 206 and 208, which are for example n-channel MOS (NMOS) transistors controlled at their gate nodes by a bias voltage $V_{gate}$ on a line 207. Transistor 206 is coupled by its main current terminals between an output terminal 209 of the antenna 202 and the gate node of a transistor 210, which is for example a p-channel MOS (PMOS) transistor. Transistor 208 is coupled by its main current terminals between an output terminal 211 of the antenna 202 and the gate of a transistor 212, which is for example a PMOS transistor. The source nodes of transistors 210 and 212 are coupled to the supply voltage $V_{DD}$ via the main current terminals of a transistor 214, which receives at its gate node a row selection signal $R_{SEL}$ from the row decoder 106 of FIG. 1.

The drain of transistor 210 is coupled to a first column line 216, while the drain of transistor 212 is coupled to a second column line 218. Thus the column lines 216 and 218 are both associated with a signal column of pixel circuits 104 of the pixel array 102.

The column lines 216 and 218 provide a differential electrical operation mode output, and correspond to the output 118 of one column represented in FIG. 1. These column lines 216, 218 are coupled to each pixel circuit of the column, and to ground via current sources 220 and 222 respectively of the output block 120. The output block 120 further comprises column selection transistors 224 and 226, which are for example PMOS transistors. Transistor 224 is coupled between column line 216 and an output line 228, while transistor 226 is coupled between column line 218 and an output line 230. Transistors 224 and 226 are each for example controlled by a control signal $C_{SEL}$ for example generated by block 122 of FIG. 1 and provided to the output block 120 via the lines 126. The output lines 228, 230 for example provide differential output signals $COL_{OUT+}$ and $COL_{OUT-}$, which are differential electrical operation mode outputs corresponding to two of the lines 128 at the output of the output block 120 of FIG. 1. Each output line 228, 230 is for example coupled to the input of a corresponding amplifier circuit and ADC, for example similar to the amplifier 130 and ADC 136 of FIG. 1.

The imager 100 of FIG. 1 is for example a heterodyne or homodyne imager. In other words, a frequency signal is for example mixed with the received terahertz image signal.

In the case of a homodyne imager, the frequency signal is for example substantially equal to the frequency of the terahertz image signal, for example to the frequency of an illuminating terahertz signal. For example, the scene is illuminated by a transmission at a frequency of between 600 GHz and 1 THz, and a frequency signal of the same frequency is mixed with the received terahertz image signal. For example, the scene is illuminated by a transmission at a frequency of 650 GHz, and the frequency of the frequency signal is also 650 GHz.

In the case of a heterodyne imager, the frequency signal is for example chosen to be different from the frequency of the terahertz image signal. For example, assuming that the scene is illuminated by a transmission at a frequency of between 600 GHz and 1 THz, the frequency signal has a frequency different to that of the illumination frequency by between 1 and 5 GHz. As an example, the scene could be illuminated by a transmission at a frequency of 650 GHz, and the frequency of the frequency signal is of 649 or 651 GHz.

Due at least in part to its high frequency, there is a technical difficulty in applying the frequency signal to the detector 204 of the pixel circuit. Indeed, MOS transistors have a maximum operating frequency $f_T$ above which the gain of the transistor falls very low. The frequency $f_T$ of a typical MOS transistor is at around 200 GHz for 65 nm technology, which is significantly lower than the terahertz frequency range. Furthermore, the frequency signal must be supplied to each pixel circuit on a particularly low resistance path.

As illustrated in FIG. 2, the frequency signal $f_{LO}$ from a local oscillator 232 of the frequency oscillator circuit 115 is coupled via the line 116 to an input terminal 234 of the antenna. The input terminal 234 is for example an input of the antenna usually associated with a biasing voltage of the antenna. The frequency signal for example also includes a DC bias. The terminal 234 is adapted to be of equal distance from each of the differential outputs 209, 211 of the antenna. Thus the frequency signal is applied in a balanced manner to each input of the detector 204. The combination of the antenna 202 and the detector 204 formed of the transistors 206 and 208 forms a mixer, mixing the frequency signal $f_{LO}$ with the received terahertz signal.

In one example, a single frequency oscillator circuit 115 comprising one or more oscillators 232 provides a frequency signal for all of the pixel circuits of the array. Alternatively, there may be more than one frequency oscillator circuit 115, each for example providing the frequency signal to a different group of pixel circuits.

Figure 3:
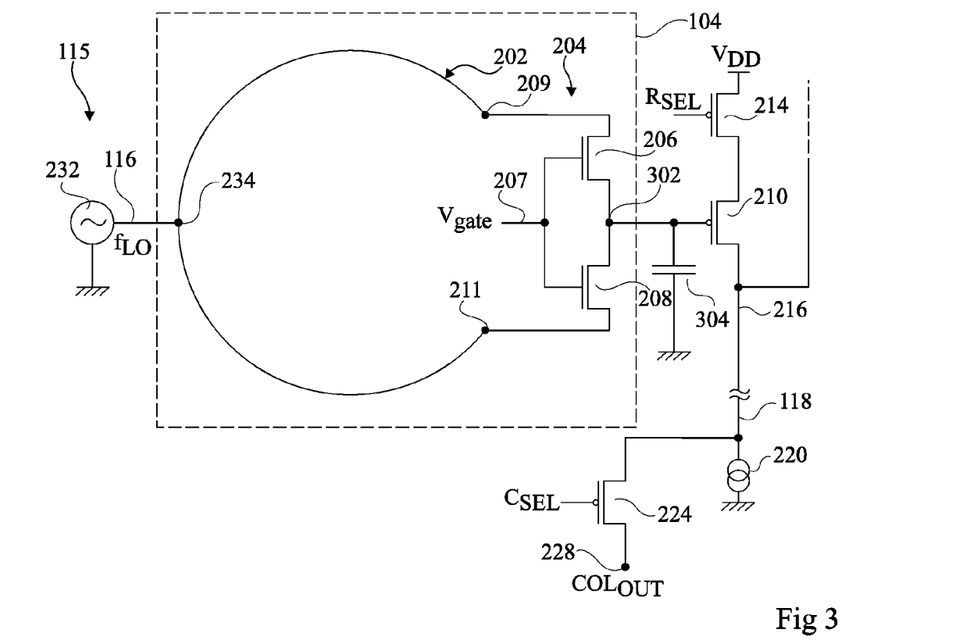
FIG. 3 illustrates a pixel circuit of a pixel array of the terahertz image sensor of FIG. 1 in more detail according to a further example embodiment of the present disclosure.

FIG. 3 illustrates the pixel circuit 104 and output circuitry according to an alternative embodiment. Those features in common with the embodiment of FIG. 2 have been labeled with like reference numerals and will not be described again in detail.

In the embodiment of FIG. 3, the transistors 206 and 208 of the detector 204 are coupled respectively between the nodes 209 and 211 of the antenna 202 and a common output node 302 of the pixel circuit. The output node 302 is coupled to a grounded capacitor 304 and also to the gate node of PMOS transistor 210. The row selection transistor 214, current source 220 and column selection transistor 224 are the same as those of the pixel circuit of FIG. 2, and will not be described again in any detail. The second set of column output components 212, 222 and 226 are not present in the pixel circuit of FIG. 3, a single output line being provided from each column.

The pixel circuit of FIG. 3 is, for example, a homodyne circuit as described above. With respect to a similar pixel circuit without an input receiving the frequency signal $f_{LO}$, the circuit of FIG. 3 is more sensitive to the terahertz image signal, which generally leads to a quality improvement.

Figure 4:
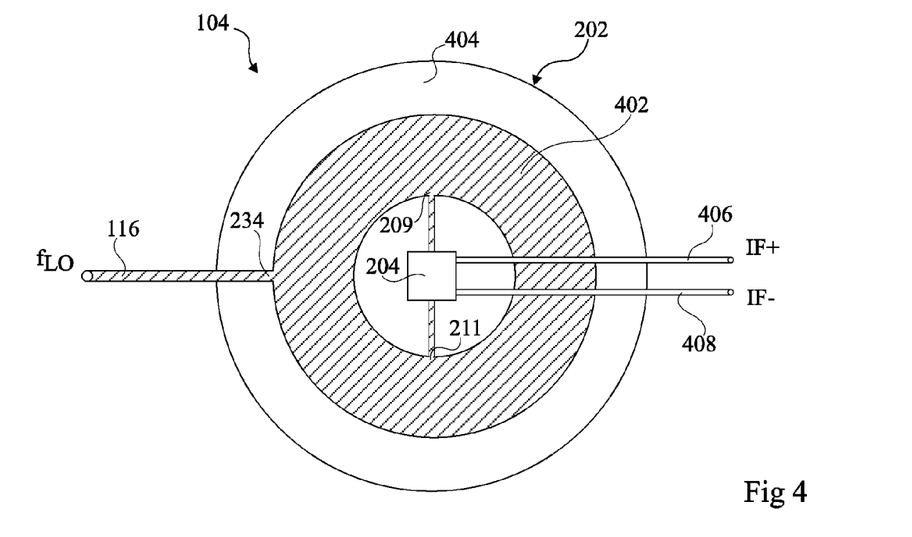
FIG. 4 illustrates in plan view an antenna of the pixel circuit of FIG. 2 according to an example embodiment of the present disclosure.

FIG. 4 is a plan view of the antenna 202 of the pixel circuit 104 of FIG. 2 in more detail. As illustrated, the antenna for example comprises an inner conductive ring 402 formed within a larger circular zone 404 of a substrate, which is for example a zone in which the substrate is covered by an epi layer blocker.

The input terminal 234 of the antenna is formed as a protrusion at a point on the outer edge of the ring 402. The frequency signal $f_{LO}$ is applied at an extremity of a conducting track 116 connected to the terminal 234.

The differential output terminals 209 and 211 of the antenna are for example formed as protrusions from the inner edge of the ring 402, on opposite sides. The points at which the output terminals 209 and 211 are formed are each at the same distance from the input terminal 234. The detector 204 is for example formed in a central zone surrounded by the ring 402. Conducting tracks 406 and 408 for example bring the differential output signals IF+ and IF− to the corresponding column lines (not illustrated in FIG. 4). In some embodiments, the transistors 210, 212 and 214 are also formed in the central zone surrounded by ring 402.

The ring 402 for example has an average diameter of between 50 and 200 μm, and the thickness of the ring between its inner and outer edges is for example between 5 and 25 μm.

The antenna of the embodiment of FIG. 3 is for example formed of the same circuit as FIG. 4, except that a single output track from the detector 204 is present.

Figure 5:
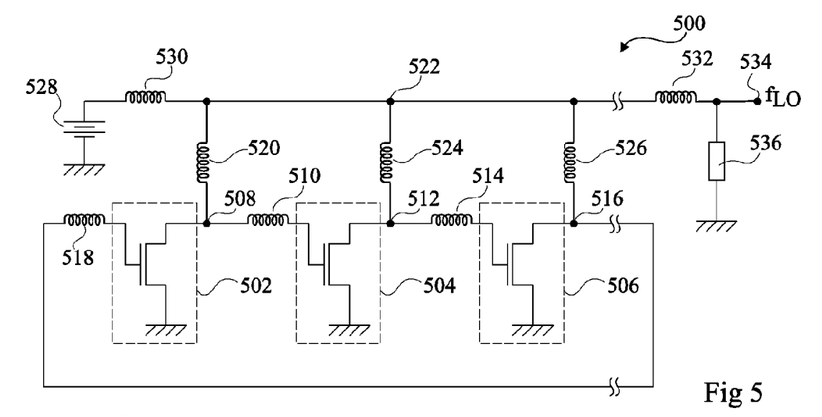
FIG. 5 illustrates a frequency oscillation circuit according to an example embodiment of the present disclosure.

FIG. 5 illustrates a frequency oscillation circuit 500 according to an example embodiment. The circuit 500 is for example used to implement the frequency oscillation circuit 115 of FIGS. 2 and 3. Alternatively, the frequency oscillator circuit 500 may have other applications, such as providing a high frequency signal for generating terahertz radiation, for example for illuminating a scene to be captured by a terahertz imager.

As indicated above, a difficulty in processing terahertz signals by MOS transistors is that the maximum operating transistor frequency $f_T$ of a MOS transistor is far lower than the terahertz frequency range.

To overcome this difficulty, the circuit 500 comprises a ring oscillator formed of an odd number of series-coupled inverters coupled in a loop, each of the inverters operating within the frequency limit of MOS technology, for example at between 150 to 200 GHz in the case of 65 nm technology. In the example of FIG. 5, three inverters are formed by NMOS transistors 502, 504 and 506. The transistor 502 is coupled between a node 508 and ground, for example having its source connected to ground, and its drain coupled to node 508. Node 508 is further coupled via an inductor 510 to the gate node of the transistor 504. Similarly, transistor 504 is coupled between a node 512 and ground, node 512 further being coupled via an inductor 514 to the gate node of transistor 506. Transistor 506 is coupled between node 516 and ground, node 516 being coupled to the gate of transistor 502 via an inductor 518.

The node 508 is further coupled via an inductor 520, or other form of band-pass filter, to a summing node 522. Similarly, nodes 512 and 516 are coupled to the summing node 522 via inductors 524 and 526 respectively, or other forms of band-pass filters. The summing node 522 is supplied by a voltage source 528 coupled to the summing node 522 via an inductor 530. For example the voltage source provides a DC bias voltage of between 0.5 and 2.5 V.

The summing node 522 is coupled via an inductor 532 to an output node 534 of the frequency oscillator circuit 500. The node 534 is also for example coupled to ground via a resistor 536.

As represented in FIG. 5, in some embodiments the chain of inverters is extended to comprise more than three inverters and corresponding inductors, for example any odd number. For example, the chain of inverters could comprise 5, 7 or 9 inverters and corresponding inductors.

Operation of the circuit 500 of FIG. 5 will now be described in more detail with reference to FIGS. 6 and 7. In this example, the inverter chain comprises three inverters.

Figure 6:
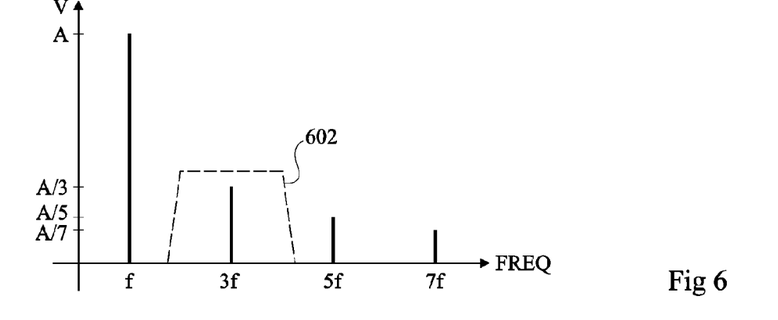
FIG. 6 is a graph representing a frequency spectrum of signals in the circuit of FIG. 5 according to an example embodiment of the present disclosure.

FIG. 6 is a graph showing a frequency spectrum of the signal present at each of the nodes 508, 512 and 516 of FIG. 5. The signal at each of these nodes is a square wave comprising various sinusoidal components. In particular, the signal is composed of a wave of amplitude A at a fundamental frequency f. The fundamental frequency depends on the number of transistors in the loop, and the delay introduced by each transistor. A typical example of such frequency could be between 150 GHz to 200 GHz. Furthermore, the signal comprises waveforms at the odd harmonic frequencies. FIG. 6 illustrates the third harmonic having an amplitude A/3, the fifth harmonic having an amplitude A/5 and the seventh harmonic having an amplitude A/7.

Assuming a fundamental frequency at between 150 and 200 GHz, the third harmonic is for example at between 450 and 600 GHz, and the fifth harmonic is for example at between 750 GHz and 1 THz. The seven harmonic is for example at between 1 THz and 1.4 THz.

Each of the inductors 520, 524 and 526, which couple the nodes 508, 514 and 516 to the summing node 522, is selected to provide a band-pass filter having the pass band centre indicated by a dashed line in FIG. 6, to select the third harmonic frequency signal. For example, in the case of selecting the third harmonic frequency, the pass band is for example between 400 and 700 GHz, and the inductors 520, 524 and 526 for example each have a value of a few pH or less.

In the more general case of a ring oscillator having N inverters, N being an odd integer equal to 3 or more, the pass bands of the filters coupling the output of each inverter to the summing node are for example chosen to select the Nth harmonic frequency. In such a ring oscillator of N inverters, the Nth harmonic has the property of being in phase at the output node of each inverter, as will now be explained with reference to FIG. 7.

Figure 7:
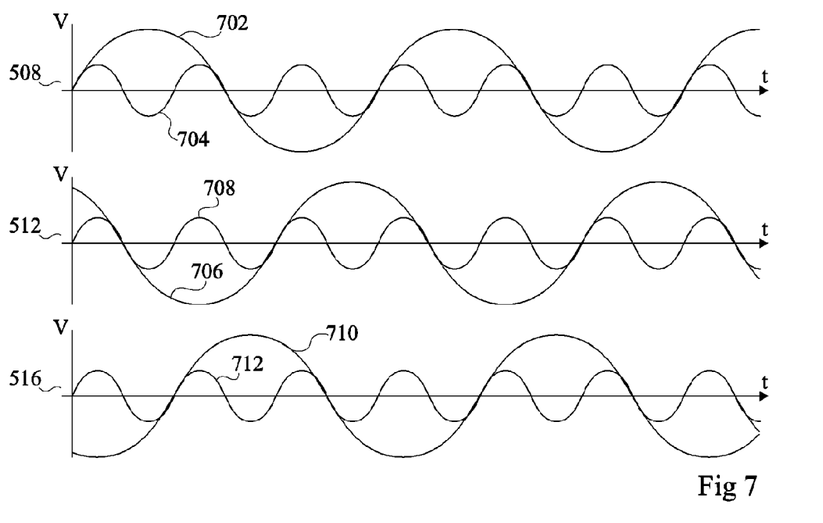
FIG. 7 illustrates signals in the circuit of FIG. 5 according to an example embodiment of the present disclosure.

FIG. 7 shows three graphs showing examples of the fundamental frequency signal 702 and Nth harmonic frequency 704 present at nodes 508, 512 and 516 respectively, for the case that N is equal to three.

As illustrated, the phase of the fundamental frequency 702 is shifted at each node with respect to the previous node by $2\pi/N$ radians, and the signal is inverted. This makes the fundamental frequency signal present at each node unsuitable for being combined. However, due to its higher frequency, the same shift in the Nth harmonic frequency (third harmonic in the example of FIG. 7) results in in-phase waveforms at each node 508, 512 and 516. Thus, the Nth harmonic frequencies adds with constructive interference to generate a signal of higher amplitude. Furthermore, the frequency of the Nth harmonic frequency is N times that of the fundamental frequency, allowing the maximum transistor frequency $f_T$ of the transistor technology to be exceeded.

Figure 8:
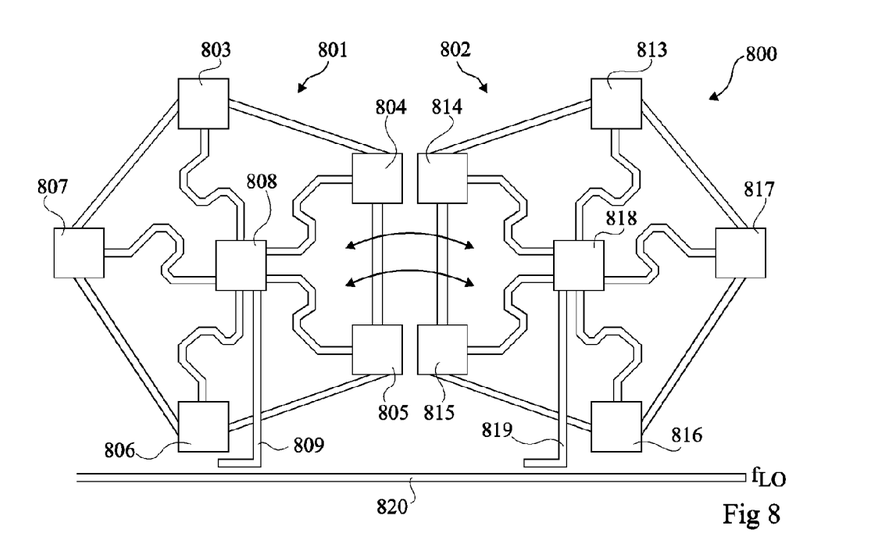
FIG. 8 illustrates a frequency oscillation layout structure according to a further example embodiment of the present disclosure.

FIG. 8 is a plan view illustrating the layout structure of a frequency oscillation circuit 800 according to a further embodiment.

In the example of FIG. 8, there are two rings oscillators 801 and 802, each formed in a similar fashion to the circuit of FIG. 5, and each comprising 5 inverters.

In particular, ring oscillator 801 comprises inverters 803, 804, 805, 806 and 807 coupled in a ring in a similar fashion to the inverters 502, 504 and 506 of FIG. 5. The connections between the inverters are formed by transmission lines, which also form the role of the inductors. Each of the inverters is further coupled by a corresponding transmission line of equal length to a node 808 forming the summing node 522 of the ring oscillator 801, these transmission lines forming inductors of the band-pass filters. A transmission line 809 from the summing node 808 provides the summed frequency signal.

Similarly, the ring oscillator 802 comprises inverters 813, 814, 815, 816 and 817 coupled in a ring in a similar fashion to the inverters 502, 504 and 506 of FIG. 5. The connections between the inverters are formed by transmission lines, which also form the role of the inductors. Each of the inverters is further coupled to a node 818 forming the summing node 522 of the ring oscillator 802. A transmission line 819 from the summing node 818 provides the summed frequency signal.

Each of the transmission lines 809, 819 is electromagnetically coupled to a common output track 820, which provides the resulting frequency signal $f_{LO}$.

In order for the frequency signal generated by each of the ring oscillators to be summed on the output track 820, they should be in-phase. To achieve this, electromagnetic coupling is provided between the ring oscillators 801, 802, and in particular between at least one of the transmission lines between inverters of each ring oscillator. In the example of FIG. 8, the transmission line coupling inverters 804 and 805 is electromagnetically coupled to the transmission line coupling inverters 814 and 815. For example, to achieve phase synchronisation, there is between −5 and −15 dB of cross-coupling between the lines. Those skilled in the art will understand how to achieve a desired level of cross-coupling, based for example on the spacing between the transmission lines.

Figure 9:
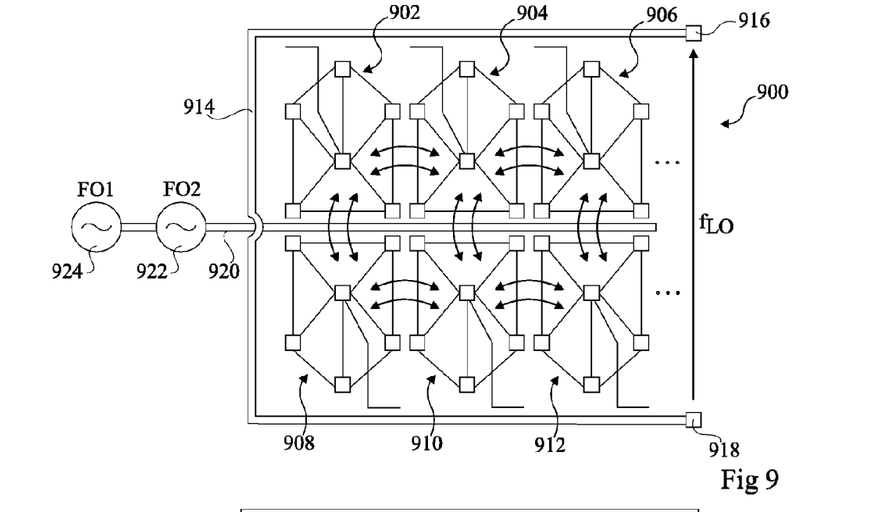
FIG. 9 illustrates a frequency oscillation circuit according to yet a further example embodiment of the present disclosure.

FIG. 9 illustrates a frequency oscillation circuit 900 according to a further embodiment. In this example, six ring oscillators 902, 904, 906, 908, 910 and 912 are each coupled in relatively close proximity. Furthermore, an output line from each of the ring oscillators 902 to 912 is electromagnetically coupled to a common conductive track 914, which for example makes a horse shoe shape surrounding the ring oscillators and provides the output frequency signal $f_{LO}$ at output terminals 916 and 918 at its respective extremities. Each of the ring oscillators is electromagnetically coupled to at least two of the other ring oscillators in similar fashion to the oscillators 801 and 802 of FIG. 8.

Optionally, a further conductive track 920 may be provided passing by a transmission line of each ring oscillator 902 to 912, such that a further oscillation frequency can be used to tune the frequency and phase oscillation of each oscillator. For example, the further oscillation frequency signal is generated by a main phase-locked and frequency-tunable oscillator 924, which locks to a further high frequency oscillator 922.

As represented by a series of dots in FIG. 9, while 6 ring oscillators are represented in FIG. 9, the principle could be extended to a greater number of oscillators.

It will be apparent to those skilled in the art that, the higher the number of ring oscillators operating in phase, the higher the output amplitude of the generated frequency signal. For example, a high amplitude signal can be beneficial for transmitting terahertz radiation to illuminate a scene, or for having enough power for the signal to be provided to all of the pixel circuits of a heterodyne or homodyne image sensor.

Figure 10:
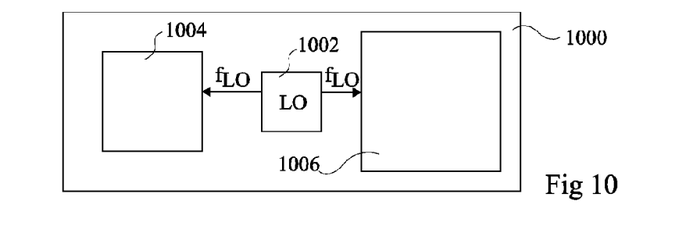
FIG. 10 illustrates a terahertz device according to an example embodiment of the present disclosure.

FIG. 10 illustrates a terahertz device 1000, which for example comprises a frequency oscillation circuit 1002 for generating a frequency signal $f_{LO}$. The frequency signal is for example provided to a transmission system 1004 for illuminating a scene and/or to a terahertz image sensor 1006 for capturing a scene using a heterodyne or homodyne imager.

An advantage of the embodiments described herein with reference to FIGS. 2, 3 and 4 is that a simple pixel circuit can be provided in which a frequency signal is mixed with a received terahertz image signal.

An advantage of the embodiments described herein with reference to FIGS. 5 to 9 is that a high frequency signal can be generated without being limited by the maximum transistor frequency $f_T$ of the transistor technology that is used.

Having thus described at least one illustrative embodiment of the invention, various alterations, modifications and improvements will readily occur to those skilled in the art.

For example, while in the embodiment of FIG. 4 an example shape and layout of an antenna has been represented, it will be apparent to those skilled in the art that various different shapes and layouts could be used.

Furthermore, while in the examples of FIGS. 5 to 9 the output of each inverter of each ring oscillator is summed to generate the output signal, it would be possible to sum only the output taken from two or more of the inverters. However, there is of course an interest in summing the maximum number of signals if the objective is to generate an output signal of the highest amplitude.

What is claimed is:

1. A terahertz imager comprising:
an array of pixel circuits, each pixel circuit comprising
a differential output antenna comprising a first output terminal, a second output terminal, and an input terminal, and
a detector circuit comprising
a first transistor having a first conduction terminal coupled to the first output terminal, a second conduction terminal, and a control terminal coupled to a dedicated bias voltage input terminal,
a second transistor having a first conduction terminal coupled to the second output terminal, a second conduction terminal, and a control node coupled to the dedicated bias voltage input terminal,
a third transistor having a first conduction terminal coupled to a supply terminal, a second conduction terminal coupled to a first differential electrical output terminal, and a control terminal coupled to the second conduction terminal of the first transistor, and
a fourth transistor having a first conduction terminal coupled to the supply terminal, a second conduction terminal coupled to a second differential electrical output terminal, and a control terminal coupled to the second conduction terminal of the second transistor; and
a frequency oscillator configured to generate a frequency signal on an output line, the output line being coupled to the input terminal of the differential output antenna of at least one of the pixel circuits.

2. The terahertz imager of claim 1, wherein the frequency oscillator comprises a ring oscillator having a plurality of inverters.

3. The terahertz imager of claim 1, wherein:
the second conduction terminal of the first transistor is directly connected to the control terminal of the third transistor, and
the second conduction terminal of the second transistor is directly connected to the control terminal of the fourth transistor.

4. The terahertz imager of claim 1, wherein:
the first conduction terminal of the first transistor is directly connected to the first output terminal, and
the first conduction terminal of the second transistor is directly connected to the second output terminal.

5. The terahertz imager of claim 1, wherein:
the control terminal of the first transistor is directly connected to the dedicated bias voltage input terminal, and
the control terminal of the second transistor is directly connected to the dedicated bias voltage input terminal.

6. The terahertz imager of claim 1, wherein the detector circuit further comprises a select transistor, the select transistor coupling the first conduction terminal of the third transistor and the first conduction terminal of the fourth transistor to the supply terminal, wherein a control terminal of the select transistor is coupled to a row selection terminal configured to receive a row selection signal.

7. The terahertz imager of claim 6, wherein the detector circuit further comprises:
a first output transistor having a first conduction terminal coupled to the first differential electrical output terminal, a second conduction terminal coupled to a first column output terminal, and a control terminal coupled to a column selection terminal configured to receive a column selection signal,
a second output transistor having a first conduction terminal coupled to the second differential electrical output terminal, a second conduction terminal coupled to a second column output terminal, and a control terminal coupled to the column selection terminal,
a first current source having a first conduction terminal coupled to the first differential electrical output terminal and a second conduction terminal coupled to a reference terminal, and a second current source having a first conduction terminal coupled to the second differential electrical output terminal and a second conduction terminal coupled to the reference terminal.

8. The terahertz imager of claim 1, wherein the differential output antenna comprises an annular conductor, the first output terminal and the second output terminal being positioned at opposite points around the annular conductor and the input terminal being positioned at a point between the first output terminal and the second output terminal.

9. The terahertz imager of claim 8, wherein the input terminal is positioned at a point of equal distance from the first output terminal and the second output terminal.

10. The terahertz imager of claim 9, wherein the first output terminal and the second output terminal are positioned on an inner edge of the annular conductor and the input terminal is positioned on an outer edge of the annular conductor.

11. The terahertz imager of claim 1, wherein the first transistor is an n-type transistor, the second transistor is an n-type transistor, the third transistor is a p-type transistor, and the fourth transistor is a p-type transistor.

12. A terahertz imager comprising:
an array of pixel circuits, each pixel circuit comprising
a differential output antenna comprising a first output terminal, a second output terminal, and an input terminal, and
a detector circuit comprising
a first transistor having a first conduction terminal coupled to the first output terminal, a second conduction terminal, and a control terminal coupled to a dedicated bias voltage input terminal,
a second transistor having a first conduction terminal coupled to the second output terminal, a second conduction terminal, and a control node coupled to the dedicated bias voltage input terminal, and
a third transistor having a first conduction terminal coupled to a supply terminal, a second conduction terminal coupled to an electrical output terminal, and a control terminal coupled to the second conduction terminal of the first transistor and coupled to the second conduction terminal of the second transistor, and
a capacitor coupled to the control terminal of the third transistor; and
a frequency oscillator configured to generate a frequency signal on an output line, the output line being coupled to the input terminal of the differential output antenna of at least one of the pixel circuits.

13. The terahertz imager of claim 12, wherein:
the first conduction terminal of the first transistor is directly connected to the first output terminal,
the first conduction terminal of the second transistor is directly connected to the second output terminal,
the second conduction terminal of the first transistor is directly connected to the control terminal of the third transistor, and
the second conduction terminal of the second transistor is directly connected to the control terminal of the third transistor.

14. The terahertz imager of claim 12, wherein:
the control terminal of the first transistor is directly connected to the dedicated bias voltage input terminal, and
the control terminal of the second transistor is directly connected to the dedicated bias voltage input terminal.

15. The terahertz imager of claim 12, wherein the detector circuit further comprises:
a select transistor, the select transistor coupling the first conduction terminal of the third transistor to the supply terminal, wherein a control terminal of the select transistor is coupled to a row selection terminal configured to receive a row selection signal,
an output transistor having a first conduction terminal coupled to the electrical output terminal, a second conduction terminal coupled to a column output terminal, and a control terminal coupled to a column selection terminal configured to receive a column selection signal, and
a current source having a first conduction terminal coupled to the electrical output terminal and a second conduction terminal coupled to a reference terminal.

16. The terahertz imager of claim 12, wherein the differential output antenna comprises an annular conductor, the first output terminal and the second output terminal being positioned at opposite points around the annular conductor and the input terminal being positioned at a point between the first output terminal and the second output terminal.

17. The terahertz imager of claim 16, wherein the input terminal is positioned at a point of equal distance from the first output terminal and the second output terminal.

18. The terahertz imager of claim 17, wherein the first output terminal and the second output terminal are positioned on an inner edge of the annular conductor and the input terminal is positioned on an outer edge of the annular conductor.

19. The terahertz imager of claim 12, wherein the first transistor is an n-type transistor, the second transistor is an n-type transistor, and the third transistor is a p-type transistor.

20. A terahertz imager comprising:
an array of pixel circuits, each pixel circuit comprising
a differential output antenna comprising
an annular conductive ring overlying a substrate having a central open region,
an input conductive track attached to an outer edge of the annular conductive ring,
a first internal conductive track attached to an inner edge of the annular conductive ring, and
a second internal conductive track attached to the inner edge of the annular conductive ring, and
a detector circuit comprising
a first transistor formed within the central open region and having a conduction path from the first internal conductive track to a first internal control terminal and having a control terminal coupled to a dedicated bias voltage input terminal,
a second transistor formed within the central open region and having a conduction path from the second internal conductive track to a second internal control terminal and having a control node coupled to the dedicated bias voltage input terminal; and
a frequency oscillator configured to generate a frequency signal on an output line, the output line being coupled to the input conductive track of the differential output antenna of at least one of the pixel circuits.

21. The terahertz imager of claim 20, wherein the detector circuit further comprises:
a third transistor having a first conduction terminal coupled to a supply terminal, a second conduction terminal coupled to a first differential electrical output terminal, and a control terminal coupled to the first internal control terminal; and a fourth transistor having a first conduction terminal coupled to the supply terminal, a second conduction terminal coupled to a second differential electrical output terminal, and a control terminal coupled to the second internal control terminal.

22. The terahertz imager of claim 21, wherein the differential output antenna further comprises a first output conductive track and a second output conductive track formed in the central open region and extending outside the annular conductive ring, and the first differential electrical output terminal is coupled to the first output conductive track and the second differential electrical output terminal is coupled to the second output conductive track.

23. The terahertz imager of claim 20, wherein the detector circuit further comprises a third transistor having a first conduction terminal coupled to a supply terminal, a second conduction terminal coupled to an electrical output terminal, and a control terminal coupled to the first internal control terminal and the second internal control terminal.

24. The terahertz imager of claim 23, wherein the differential output antenna further comprises an output conductive track formed in the central open region and extending outside the annular conductive ring, and the electrical output terminal is coupled to the output conductive track.

25. The terahertz imager of claim 20, wherein the differential output antenna further comprises an epi layer blocker formed overlying the substrate and underlying the annular conductive ring.

26. The terahertz imager of claim 20, wherein the input conductive track is positioned at a point of equal distance from the first internal conductive track and the second internal conductive track.

* * * * *